US006993391B2

(12) United States Patent
Flesler et al.

(10) Patent No.: US 6,993,391 B2
(45) Date of Patent: Jan. 31, 2006

(54) ACUTE AND CHRONIC ELECTRICAL SIGNAL THERAPY FOR OBESITY

(75) Inventors: Melina Flesler, Misgav (IL); Yuval Mika, Zichron Yaakov (IL); Ziv Belsky, Haifa (IL); Yaakov Ben Arie, Haifa (IL); Nissim Darvish, Tzrufa (IL); Shlomo Ben-Haim, Cesarea (IL)

(73) Assignee: Metacure N.V., Curacao (AN)

( * ) Notice: Subject to any disclaimer, the term of this patent is extended or adjusted under 35 U.S.C. 154(b) by 157 days.

(21) Appl. No.: 10/446,567

(22) Filed: May 28, 2003

(65) Prior Publication Data

US 2004/0044376 A1 Mar. 4, 2004

Related U.S. Application Data

(63) Continuation of application No. 09/734,358, filed on Dec. 11, 2000, now Pat. No. 6,600,953.

(51) Int. Cl.
*A61N 1/18* (2006.01)
(52) U.S. Cl. ...................................................... 607/40
(58) Field of Classification Search ................... 607/40
See application file for complete search history.

(56) References Cited

U.S. PATENT DOCUMENTS

| | | | |
|---|---|---|---|
| 3,411,507 A | 11/1968 | Wingrove | 607/40 |
| 5,074,868 A | 12/1991 | Kuzmak | 606/157 |
| 5,188,104 A | 2/1993 | Wernicke et al. | 607/40 |
| 5,226,429 A | 7/1993 | Kuzmak | 128/898 |
| 5,234,454 A | 8/1993 | Bangs | 606/191 |
| 5,263,480 A | 11/1993 | Wernicke et al. | 607/118 |
| 5,423,872 A | 6/1995 | Cigaina | 607/40 |
| 5,449,368 A | 9/1995 | Kuzmak | 606/157 |
| 5,601,604 A | 2/1997 | Vincent | 606/216 |
| 5,690,691 A | 11/1997 | Chen et al. | 607/40 |
| 5,716,385 A | 2/1998 | Mittal et al. | 607/40 |
| 5,836,994 A | 11/1998 | Bourgeois | 607/40 |
| 5,991,649 A | 11/1999 | Garfield et al. | 600/372 |
| 6,026,326 A | 2/2000 | Bardy | 607/40 |
| 6,067,991 A | 5/2000 | Forsell | 128/899 |
| 6,091,992 A | 7/2000 | Bourgeois et al. | 607/40 |
| 6,097,984 A * | 8/2000 | Douglas | 607/40 |
| 6,104,955 A | 8/2000 | Bourgeois | 607/40 |
| 6,243,607 B1 | 6/2001 | Mintchev et al. | 607/40 |
| 6,449,511 B1 | 9/2002 | Mintchev et al. | 607/40 |
| 6,591,137 B1 | 7/2003 | Fischell et al. | 607/40 |
| 2003/0009202 A1 | 1/2003 | Levine | 607/58 |
| 2004/0059393 A1 * | 3/2004 | Policker et al. | 607/40 |

FOREIGN PATENT DOCUMENTS

| | | |
|---|---|---|
| WO | WO 97/25098 | 7/1997 |
| WO | WO 99/03533 | 1/1999 |
| WO | WO 02/26101 | 4/2002 |

* cited by examiner

*Primary Examiner*—Carl Layno
(74) *Attorney, Agent, or Firm*—Wolf, Block, Schorr & Solis-Cohen LLP; William H. Dippert (57) ABSTRACT

Apparatus is provided for treating a condition such as obesity. The apparatus includes a set of one or more electrodes, which are adapted to be applied to one or more respective sites in a vicinity of a body of a stomach of a patient. A control unit is adapted to drive the electrode set to apply to the body of the stomach a signal, configured such that application thereof increases a level of contraction of muscle tissue of the body of the stomach, and decreases a cross-sectional area of a portion of the body of the stomach for a substantially continuous period greater than about 3 seconds.

38 Claims, 6 Drawing Sheets

ACUTE AND CHRONIC ELECTRICAL SIGNAL THERAPY FOR OBESITY

CROSS-REFERENCE TO RELATED APPLICATIONS

This patent application is a continuation of commonly assigned U.S. patent application Ser. No. 09/734,358, filed Dec. 11, 2000, now U.S. Pat. No. 6,600,953.

FIELD OF THE INVENTION

The present invention relates generally to treatment of obesity, and specifically to invasive techniques and apparatus for treating obesity.

BACKGROUND OF THE INVENTION

Invasive treatments for obesity are often recommended for patients with a body mass index (mass/height$^2$ [kg/m$^2$]) which is greater than 35 or 40. For such patients, their weight is commonly associated with increased risk of heart disease, diabetes, and arthritis. Preferably, the invasive treatments are accompanied by changes in lifestyle, such as improved eating habits and an appropriate exercise regimen.

U.S. Pat. No. 6,067,991 to Forsell, U.S. Pat. No. 5,601,604 to Vincent, and U.S. Pat. No. 5,234,454 to Bangs, and U.S. Pat. Nos. 5,449,368, 5,226,429 and 5,074,868 to Kuzmak, which are incorporated herein by reference, describe mechanical instruments for implantation in or around the stomach of an obese patient.

U.S. Pat. No. 5,690,691 to Chen et al., which is incorporated herein by reference, describes a gastric pacemaker for treating obesity and other conditions. The pacemaker includes multiple electrodes which are placed at various positions on the gastrointestinal (GI) tract, and which deliver phased electrical stimulation to pace peristaltic movement of material through the GI tract.

U.S. Pat. No. 5,423,872 to Cigaina, which is incorporated herein by reference, describes apparatus for applying electrical pulses to the distal gastric antrum of a patient, so as to reduce the motility of the stomach and to thereby treat obesity or another condition.

U.S. Pat. Nos. 5,188,104 and 5,263,480 to Wernicke et al., which are incorporated herein by reference, describe a method for stimulating the vagus nerve of a patient so as to alleviate an eating disorder.

U.S. Pat. Nos. 6,104,955, 6,091,992, and 5,836,994 to Bourgeois, U.S. Pat. No. 6,026,326 to Bardy, and U.S. Pat. No. 3,411,507 to Wingrove, which are incorporated herein by reference, describe the application of electrical signals to the GI tract to treat various physiological disorders.

PCT Patent Publication WO 99/03533 to Ben-Haim et al., entitled, "Smooth muscle controller," and U.S. patent application Ser. No. 09/481,253 in the national phase thereof, both of which are assigned to the assignee of the present patent application and are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). Use of an ETC signal is described with respect to treating obesity, by applying the ETC signal to the stomach so as to delay or prevent emptying of the stomach. In addition, a method is described for increasing the motility of the gastrointestinal tract, by applying an ETC signal to a portion of the tract in order to increase the contraction force generated in the portion.

PCT Patent Publication WO 97/25098, to Ben-Haim et al., entitled "Electrical muscle controller," and the corresponding U.S. patent application Ser. No. 09/101,723, which are assigned to the assignee of the present patent application and are incorporated herein by reference, describe methods for modifying the force of contraction of a heart chamber by applying an ETC signal to the heart.

SUMMARY OF THE INVENTION

It is an object of some aspects of the present invention to provide improved apparatus and methods for treatment of medical conditions which relate to the gastrointestinal tract.

It is a further object of some aspects of the present invention to provide improved apparatus and methods for treating obesity.

In preferred embodiments of the present invention, apparatus for treating a condition such as obesity comprises a set of one or more electrodes which are applied to one or more sites of the gastrointestinal (GI) tract of a patient. A control unit preferably drives the electrode set to apply an Excitable-Tissue Control (ETC) signal to the GI tract, so as to modulate contraction of muscles of the gastrointestinal tract and to thereby treat the condition.

In a preferred embodiment, the electrodes are applied to the stomach, and the control unit drives the electrodes to apply an enhancement signal which includes, as appropriate, the ETC signal and/or an excitatory signal. Thus, the enhancement signal may induce contractions and/or increase or otherwise modify the contraction forces generated by muscles of the stomach.

For some applications, the enhancement signal is applied so as to modify a contraction pattern of some of the stomach's muscles, in order to reduce the cross-sectional area of a portion of the stomach. The narrow ring thereby generated reduces the volume of a region of the stomach, and increases the sensation of satiety felt by the patient compared to that which would be felt without the application of this embodiment of the invention. For example, the enhancement signal may cause an "indenting" of the stomach wall, whereby food is limited in its ability to vacate the esophageal region of the stomach. Consequently, this portion of the stomach is stretched more than usual for the volume of food ingested, and an earlier sensation of satiety is induced. This embodiment thus employs electrical signals to cause a narrowing of the stomach analogous to that produced mechanically by the gastric bands described in the Background section of the present patent application. Unlike these prior art mechanical bands, however, this application of the present invention allows the extent of the narrowing to be moderated in real time by the control unit without mechanical intermediaries (e.g., modulation of fluid pressure).

Alternatively or additionally, the enhancement signal is applied, prior to and/or during a meal, so as to reduce the overall size of the stomach, thereby increasing the tension in the wall of the stomach when food is in the stomach. This increased tension typically yields a corresponding increase in the patient's sensation of satiety, and thus substantially reduces the likelihood of the patient overeating.

Further alternatively or additionally, repeated application of the enhancement signal engenders a long-term shortening of muscle fibers of the stomach, and, consequently, a reduction of the size of the stomach, even at times when the signal is not being applied. Thus, for example, the enhancement signal may be applied, intermittently throughout the day, over a period of days, weeks, or months, so as to induce desired structural changes in the stomach which last, preferably, for at least several days or weeks after removal of the signal. Advantageously, due to the stomach's reduced size, it is typically stretched during and after a meal to a greater extent than would occur without application of the enhancement signal, and thus greater sensations of satiety are felt by the patient. Optionally, the signal may be applied when the patient's stomach is expected to be relatively empty (e.g., each morning for one hour prior to the patient waking up), so as to maximize the extent to which the muscle fibers are able to shorten in response to the signal.

For some patients, it is desirable to apply the enhancement signal according to a schedule, whereby constriction of the stomach induces a feeling of satiety at times when the patient might choose to eat but should not be eating. At other times, e.g., when the patient is sleeping, the signal is typically not applied. Alternatively or additionally, the enhancement signal is (a) applied during one or more meals during the day, so as to reduce the patient's appetite during those meals, and (b) removed during meals eaten during the remainder of the day, so as to prevent nutritional deficiencies which might occur in some patients from any inappropriate, excessive use of the signals described herein.

In a preferred embodiment, the enhancement signal is applied to muscle in one portion of the stomach, so as to induce and/or modify a contraction of the stimulated muscle which, in turn, causes stretching of stretch-receptors in an adjacent portion of the stomach. This form of contraction-mediated stretching simulates the normal satiety signaling of the stomach's stretch-receptors, without the patient having eaten the quantities of food which would normally be required to trigger this satiety response.

Alternatively or additionally, some or all of the electrodes are placed in a vicinity of the pyloric sphincter, and the control unit drives the electrode set to apply the enhancement signal so as to increase a contraction force of the sphincter. The increased force typically reduces the sphincter's cross-section, and thereby generally extends a period of time in which partially-digested food remains in the stomach.

In a preferred embodiment, one or more electrodes are applied to or in a vicinity of respective sites of the arterial supply of the patient's small intestine. Typically, the control unit drives some or all of the electrodes to apply signals which cause a controllable level of constriction of the arteries to which these electrodes are coupled. The constriction produced thereby preferably transiently and controllably reduces the blood flow to the small intestine, and, it is believed, thereby reduces the total number of calories which are ultimately absorbed into the patient's bloodstream during and after eating a meal.

There is therefore provided, in accordance with a preferred embodiment of the present invention, apparatus for treating a condition, including:

a set of one or more electrodes, adapted to be applied to one or more respective sites in a vicinity of a stomach of a patient; and a control unit, adapted to drive the electrode set to apply an Excitable-Tissue Control (ETC) signal to the sites, configured such that application thereof decreases a cross-sectional area of at least a portion of the stomach.

Preferably, the set of one or more electrodes includes a first set of one or more electrodes, and the apparatus includes a second set of one or more electrodes, adapted to be applied to one or more respective sites in a vicinity of a pyloric sphincter of the stomach. The control unit is preferably adapted to drive the second electrode set to apply an ETC signal configured such that application thereof increases a contraction force of the sphincter and extends a period of time in which partially-digested food remains in the stomach.

Further preferably, the control unit is adapted to configure the ETC signal such that application thereof decreases the cross-sectional area of the portion of the stomach by at least 20%, for a substantially continuous period greater than about one minute.

Still further preferably, the portion of the stomach includes a first portion of the stomach, and the control unit is adapted to configure the ETC signal such that ingestion of food by the patient in conjunction with application of the ETC signal to the first portion induces stretching of a stretch-receptor in a second portion of the stomach that induces a sensation of satiety.

In a preferred embodiment, the control unit is adapted to drive the electrode set to apply the signal over a sufficient time period so as to engender a long-term structural change of the stomach.

Typically, the electrode set is adapted to be applied in contact with muscle tissue of the stomach.

The control unit is preferably adapted to configure the ETC signal such that the decreased cross-sectional area impedes passage of ingesta through the stomach.

Alternatively or additionally, the control unit is adapted to configure the ETC signal such that application thereof decreases a volume of the stomach.

In some preferred embodiments of the present invention, the control unit is adapted to configure a timing parameter of the ETC signal responsive to timing of natural gastric electrical activity. The ETC signal is typically applied as a series of biphasic pulses. Preferably, the control unit is adapted to configure the ETC signal to have a duration of at least about 1 second. Further preferably, the duration is at least about 3 seconds.

For some applications, the apparatus includes at least one stimulating electrode, and the control unit is adapted to drive the stimulating electrode to apply an excitatory signal to muscle tissue of the stomach in conjunction with driving the electrode set to apply the ETC signal. In these cases, the control unit is typically adapted to drive the stimulating electrode to apply gastric pacing pulses to the stomach.

Preferably, the control unit is adapted to receive a patient signal, input by the patient, and to drive and withhold driving the electrode set responsive to the patient signal.

The control unit is typically adapted to drive the electrode set in accordance with a schedule programmed into the control unit. For example, the control unit may be adapted to drive the electrode set during at least one meal eaten by the patient during a 24 hour period, and to withhold driving the electrode set during another meal eaten by the patient during the 24 hour period. Alternatively or additionally, the control unit is adapted to withhold driving the electrode set during time periods designated as times when the patient generally does not eat.

For some applications, the control unit is adapted to drive at least one of the electrodes to apply an excitatory pulse in conjunction with the ETC signal. Preferably, the control unit is adapted to drive the at least one electrode to apply the excitatory pulse as a biphasic pulse. Alternatively or additionally, the control unit is adapted to drive the at least one electrode to initiate applying the ETC signal at least about 100 ms following a termination of the excitatory pulse. Preferably, the control unit is adapted to drive the at least one electrode to initiate applying the ETC signal less than about 1000 ms following a termination of the excitatory pulse.

Preferably, the control unit is adapted to drive the electrode set while the patient is eating. The control unit may, for example, be adapted to receive a patient signal, input by the patient, indicative of the patient eating. In this case, the control unit is preferably adapted to receive by way of the patient signal an indication of a nutritional quality of food being eaten by the patient and to configure a parameter of the ETC signal responsive to the patient signal.

Alternatively or additionally, the apparatus includes a sensor which is adapted to convey to the control unit a signal responsive to the patient eating. As appropriate, the sensor may include a blood sugar sensor or a mechanical sensor. Alternatively or additionally, the sensor includes a sensing electrode, adapted to be coupled in a vicinity of a gastrointestinal tract of the patient. For some applications, the sensing electrode includes one of the one or more electrodes.

Preferably, the sensor is adapted to convey the signal responsive to a quantity of food ingested by the patient, and the control unit is adapted to withhold driving the electrode set, as appropriate, responsive to the quantity (e.g., if the quantity is less than a threshold quantity).

In a preferred embodiment, the control unit is adapted to configure the ETC signal such that application thereof decreases the cross-sectional area of a region of the stomach, and maintains the decreased cross-sectional area in the region for a duration greater than about 10 seconds.

In a preferred embodiment, the control unit is adapted to configure the ETC signal such that application thereof increases intra-gastric pressure, thereby inducing a sensation of satiety.

For some applications, the apparatus includes a second set of one or more electrodes, adapted to be applied to one or more respective sites in a vicinity of the lower-esophageal sphincter. The control unit is preferably adapted to drive the second electrode set to apply a signal to the sphincter, configured such that application thereof increases a contraction force generated by the sphincter.

There is further provided, in accordance with a preferred embodiment of the present invention, apparatus for treating a condition, including:

a set of one or more electrodes, adapted to be applied to one or more respective sites in a vicinity of a pyloric sphincter of a stomach of a patient; and a control unit, adapted to drive the electrode set to apply an Excitable-Tissue Control (ETC) signal to the sites, configured such that application thereof increases a contraction force of the sphincter and extends a period of time, in which partially-digested food remains in the stomach.

Preferably, the control unit is adapted to configure the ETC signal such that driving the electrode set to apply the ETC signal increases the contraction force for a substantially continuous period greater than about 1 minute.

As appropriate, the electrode set may be adapted to be applied in contact with muscle tissue of an antral portion of the stomach and/or in contact with muscle tissue of the sphincter.

There is still further provided, in accordance with a preferred embodiment of the present invention, apparatus for treating a condition, including:

a set of one or more electrodes, adapted to be applied to one or more respective sites in a vicinity of a body of a stomach of a patient; and a control unit, adapted to drive the electrode set to apply to the body of the stomach a signal configured such that application thereof increases a level of contraction of muscle tissue of the body of the stomach, and decreases a cross-sectional area of a portion of the body of the stomach for a substantially continuous period greater than about 3 seconds.

Preferably, the control unit is adapted to configure the signal such that application thereof decreases the cross-sectional area of the portion for a substantially continuous period greater than about 10 seconds.

There is yet further provided, in accordance with a preferred embodiment of the present invention, apparatus for treating a condition, including:

a set of one or more electrodes, adapted to be applied to one or more respective sites in a vicinity of a first portion of a stomach of a patient; and a control unit, adapted to drive the electrode set to apply to the portion of the stomach a signal configured such that application thereof increases a level of contraction of muscle tissue of the portion, and configured such that ingestion of food by the patient in conjunction with application of the signal induces stretching of a stretch-receptor in a second portion of the stomach.

Preferably, the control unit is adapted to drive the electrode set to apply the signal to a body of the stomach, and to configure a parameter of the signal such that the increased level of contraction of the muscle tissue impedes passage of ingesta through the stomach and increases a level of tension in a fundic wall of the stomach.

There is also provided, in accordance with a preferred embodiment of the present invention, apparatus for treating a condition, including:

a set of one or more electrodes, adapted to be applied to one or more respective sites on an arterial supply of small intestine of a patient; and a control unit, adapted to drive the electrode set to apply a signal to the sites, configured such that application thereof induces constriction of one or more arteries in the arterial supply and decreases a quantity of digestion products which are absorbed into blood of the patient from the small intestine.

Preferably, the control unit is adapted to determine an approximate time of initiation of eating, and to initiate driving the electrode set to apply the signal at least ten minutes subsequent thereto. Typically, the control unit is adapted to determine the approximate time of initiation of eating responsive to receiving a patient signal, input by the patient.

In a preferred embodiment, the apparatus includes a sensor which is adapted to convey to the control unit a signal indicative of food being in a gastrointestinal tract of the patient.

There is additionally provided, in accordance with a preferred embodiment of the present invention, apparatus for treating a condition, including:

a set of one or more electrodes, adapted to be applied to one or more respective sites of a stomach of a patient; and a control unit, adapted to drive the electrode set to apply to the stomach, over a sufficient time period, a sequence of pulses configured so as to engender a long-term structural change of the stomach.

Preferably, the control unit is adapted to configure the sequence of pulses as an Excitatory-Tissue Control (ETC) signal. Alternatively or additionally, the control unit is adapted to configure a parameter of the sequence of pulses such that the application of the pulses over the time period is such as to engender a continuation of the structural change for at least two days following a termination of the application of the pulses.

Preferably, the control unit is adapted to configure a parameter of the sequence of pulses such that the application of the pulses over the time period is such as to reduce a characteristic length of muscle fibers of the stomach. Alternatively or additionally, the control unit is adapted to configure a parameter of the sequence of pulses such that the application of the pulses over the time period is such as to reduce a characteristic size of the stomach.

For some applications, the control unit is adapted to drive the electrode set to apply the pulses for at least two days. Preferably, the control unit is adapted to drive the electrode set to apply the pulses for at least two weeks.

In a preferred embodiment, the control unit is adapted to drive the electrode set in accordance with a schedule programmed into the control unit. For example, the control unit may be adapted to drive the electrode set at times when the patient's stomach is generally empty, or during a meal eaten by the patient.

There is yet additionally provided, in accordance with a preferred embodiment of the present invention, a method for treating a condition, including:

applying an Excitable-Tissue Control (ETC) signal to one or more sites in a vicinity of a stomach of a patient; and configuring the ETC signal such that application thereof to the one or more sites decreases a cross-sectional area of at least a portion of the stomach.

There is still additionally provided, in accordance with a preferred embodiment of the present invention, a method for treating a condition, including:

applying an Excitable-Tissue Control (ETC) signal to one or more sites in a vicinity of a pyloric sphincter of a stomach of a patient; and configuring the ETC signal such that application thereof to the one or more sites increases a contraction force of the sphincter and extends a period of time in which partially-digested food remains in the stomach.

There is also provided, in accordance with a preferred embodiment of the present invention, a method for treating a condition, including:

applying a signal to one or more sites in a vicinity of a body of a stomach of a patient; and configuring the signal such that application thereof to the one or more sites increases a level of contraction of muscle tissue of a portion of the body of the stomach, and decreases a cross-sectional area of the portion for a substantially continuous period greater than about 3 seconds.

There is further provided, in accordance with a preferred embodiment of the present invention, a method for treating a condition, including:

applying a signal to one or more sites in a vicinity of a first portion of a stomach of a patient; and configuring the signal such that the application thereof increases a level of contraction of muscle tissue of the portion and stretches a stretch-receptor in a second portion of the stomach.

There is still further provided, in accordance with a preferred embodiment of the present invention, a method for treating a condition, including:

applying a signal to one or more sites on an arterial supply of small intestine of a patient; and configuring the signal such that application thereof to the sites induces constriction of one or more arteries in the arterial supply and decreases a quantity of digestion products which are absorbed into blood of the patient from the small intestine.

There is yet further provided, in accordance with a preferred embodiment of the present invention, a method for treating a condition, including:

applying a sequence of pulses over a time period to one or more sites of a stomach of a patient; and configuring the sequence of pulses such that application thereof to the one or more sites engenders a long-term structural change of the stomach.

The present invention will be more fully understood from the following detailed description of the preferred embodiments thereof, taken together with the drawings, in which:

DETAILED DESCRIPTION OF PREFERRED EMBODIMENTS

Figure 1A:
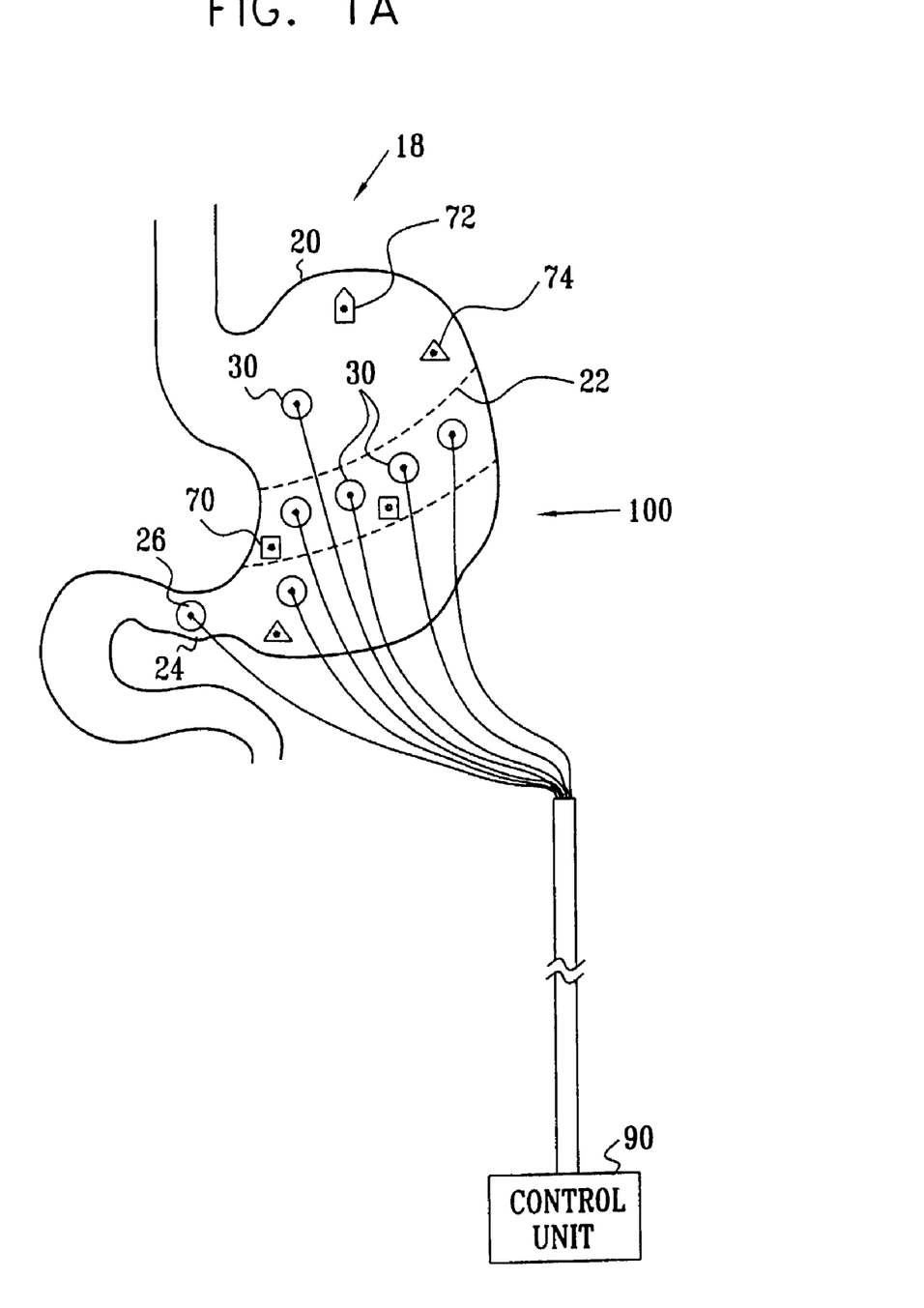
FIG. 1A is a schematic illustration of a stomach, showing the placement of electrodes and sensors thereon, in accordance with a preferred embodiment of the present invention.
Figure 1B:
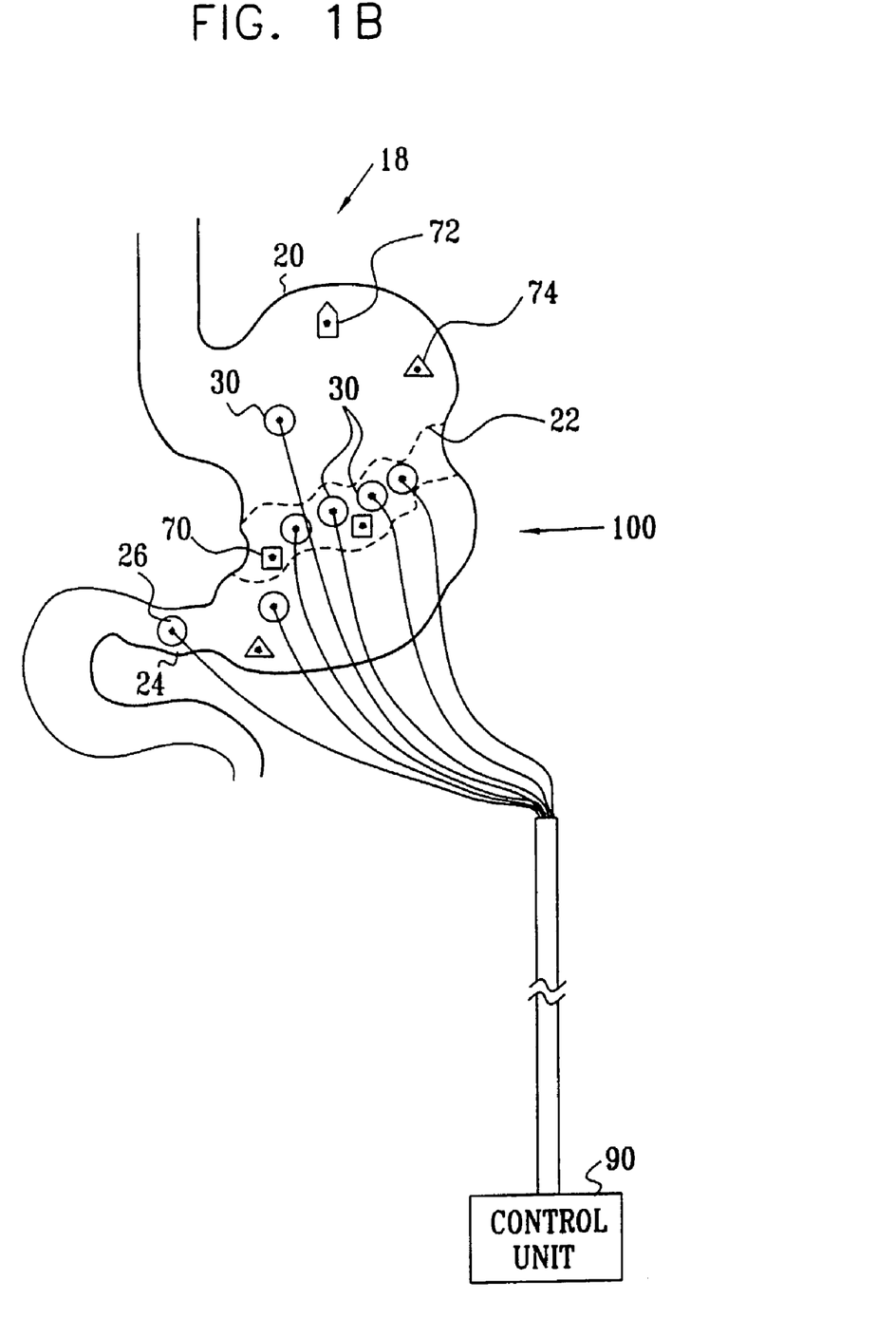
FIG. 1B is a schematic illustration of the stomach of FIG. 1A, in a contracted state thereof responsive to the application of an electrical signal thereto, in accordance with a preferred embodiment of the present invention.

Reference is now made to FIGS. 1A and 1B. FIG. 1A is a schematic illustration of gastric control apparatus 18, which applies electrical energy to modify the activity of a portion of the gastrointestinal tract of a patient, in accordance with a preferred embodiment of the present invention. Apparatus 18 typically comprises an implantable or external control unit 90, which drives one or more electrodes 100 to apply an enhancement signal to respective sites on or in a vicinity of the patient's stomach 20 and/or elsewhere on or in a vicinity of sites on the gastrointestinal tract. At least some of the sites are preferably located on the body of the stomach, i.e., that portion of the stomach located between the lower-esophageal sphincter and the pyloric sphincter. The enhancement signal is preferably configured so as to modulate contraction of muscles of the stomach and to thereby treat a condition such as obesity. FIG. 1B is a schematic illustration of stomach 20 in a contracted state thereof, responsive to the application of the enhancement signal thereto in accordance with a preferred embodiment of the present invention.

Preferably, the enhancement signal includes, as appropriate, an Excitable-Tissue Control (ETC) signal and/or an excitatory signal which induces contraction of muscles of the stomach. Aspects of ETC signal application are typically performed in accordance with techniques described in the above-referenced PCT Publications WO 99/03533 and WO 97/25098 and their corresponding U.S. national phase application Ser. Nos. 09/481,253 and 09/101,723, mutatis mutandis. For some applications, the ETC signal is applied responsive to natural electrical activity of stomach 20, for example, after a designated delay following a detected activation of a portion of the stomach. For these applications, it is preferable to use apparatus and methods described in Israel Patent Application 129,257, entitled "Trigger-based regulation of excitable tissue control in the heart," mutatis mutandis. This application is assigned to the assignee of the present invention and is incorporated herein by reference. Alternatively, the ETC signal is applied subsequent to an artificial gastric pacing pulse, as described hereinbelow.

Typically, control unit 90 drives electrodes 100 to apply the enhancement signal so as to create a contraction pattern of some of the muscles of stomach 20, such as the contraction shown in FIG. 1B, in order to reduce the cross-sectional area of a portion 22 of the stomach. This reduction is believed to increase the sensation of satiety felt by the patient compared to that which was felt prior to application of the enhancement signal. Typically, the enhancement signal is configured such that the cross-sectional area of the stomach is reduced by at least 20%, and this reduction is maintained in one region of the stomach for a period of at least 1 minute. It is to be understood that for some applications, greater or lesser reductions in cross-sectional area may be desirable, and these may be maintained for periods greater or less than 1 minute.

Electrodes 100 preferably comprise one or more signal application electrodes 30, which may also operate in a sensing mode. In addition, one or more dedicated local sense electrodes 74 are preferably placed on or in stomach 20, and convey electrical signals to control unit 90 responsive to natural gastric electric activity. Further preferably, one or more mechanical sensors 70 (e.g., accelerometers, force transducers, strain gauges, or pressure gauges) are coupled to the control unit and are placed on or in the stomach. Alternatively or additionally, one or more supplemental sensors 72 (e.g., pH sensors, blood sugar sensors, intragastric pressure sensors and/or sonometric sensors) are coupled to the control unit and are placed on or in the gastrointestinal tract or elsewhere on or in the patient's body. The control unit preferably modifies the waveform applied through electrodes 100 responsive to signals from sensors 70 and 72 and local sense electrodes 74, as described hereinbelow with reference to FIG. 2. Typically, control unit 90 and the above-mentioned electrodes and sensors are permanently or semi-permanently implanted in or coupled to the patient's body. (For clarity, connections between control unit 90 and only some of the electrodes and sensors are shown in FIG. 1A.)

Electrodes 100 are typically coupled to the serosal layer of the stomach and/or inserted into the muscular layer of the stomach. Alternatively or additionally, the electrodes are coupled elsewhere on the stomach, gastrointestinal tract, or to other suitable locations in or on the patient's body. The number of electrodes and sensors, as well as the positions thereof, are shown in FIG. 1A by way of example, and other sites on stomach 20 or in a vicinity thereof are appropriate for electrode and sensor placement in other applications of the present invention. Different types of electrodes known in the art are typically selected based Son the specific manifestation of the patient's condition, and may comprise stitch, coil, screw, patch, basket, needle and/or wire electrodes, or substantially any other electrode known in the art of electrical stimulation or sensing in tissue.

Preferably, control unit 90, electrodes 100, and the various sensors described herein are implanted in the patient in a manner generally similar to that used to implant gastric pacemakers or other apparatus for stimulating the gastrointestinal tract which are known in the art. As appropriate, techniques described in one or more of the patents cited in the Background section of the present patent application may be adapted for use with these embodiments of the present invention.

Figure 2:
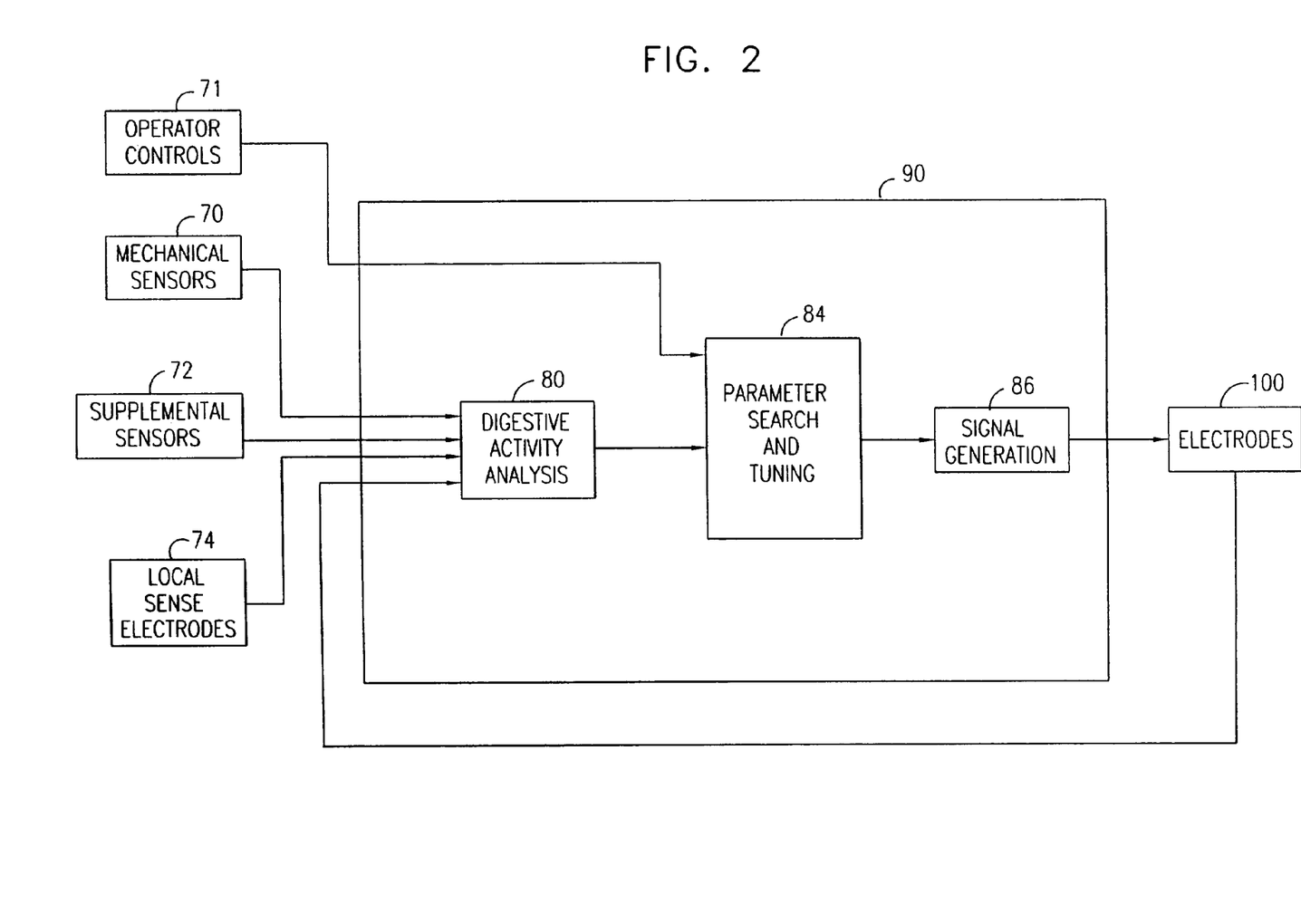
FIG. 2 is a schematic block diagram of a control unit, which generates signals to be applied to the electrodes shown in FIG. 1A, in accordance with a preferred embodiment of the present invention.

FIG. 2 is a schematic block diagram of control unit 90, in accordance with a preferred embodiment of the present invention. Mechanical sensors 70, supplemental sensors 72, local sense electrodes 74, and electrodes 100 are preferably coupled to provide feedback signals to a digestive activity analysis block 80 of control unit 90. The feedback signals generally provide block 80 with information about various aspects of the stomach's present state (e.g., empty or full) and the stomach's level of activity, so as to enable block 80 to analyze the signals and actuate control unit 90 to modify the electrical energy applied to electrodes 100 responsive to the analysis. Preferably, the enhancement signal is adjusted by the control unit responsive to the feedback signals in order to yield a desired response, e.g., an indication by mechanical sensors 70 of a desired level of muscle contraction within portion 22, or an indication by supplemental sensors 72 of maintenance of the patient's blood sugar level within a desired range. Advantageously, the ability to turn the enhancement signal on or off at any time, in order to modulate the stomach's shape, provides a generally safer and more effective alternative to prior art, purely-mechanical techniques for remodeling the stomach.

For some applications, control unit 90 drives electrodes 100 to apply the enhancement signal according to a schedule, so as to induce constriction of stomach 20 at times when the patient should not be eating, or when the patient's eating should be minimized. Alternatively or additionally, the enhancement signal is (a) applied during one or more meals during the day, so as to reduce the patient's appetite during those meals, and (b) removed during the remainder of the day, so as to prevent counterproductive remodeling of the stomach.

Alternatively or additionally, the patient activates, deactivates, and modulates the level of signal application in accordance with physician's instructions, aspects of the patient's diet, or other factors. For example, the patient may eat soup and salad at dinner, and then activate the control unit using operator controls 71, so as to increase the sense of satiety prior to being presented with a large selection-of high-calorie options for an entree. The patient may subsequently input a command for a higher level of signal-application during dessert, such that the patient will feel very full, and, in fact, not have space for the dessert. It is seen through this example that this embodiment of the present invention can be used to encourage the patient to fully satisfy all nutritional needs, while simultaneously reducing or eliminating the hunger sensation which the patient would otherwise feel if stomach 20 were not in the contracted state induced by the enhancement signal.

For some applications, control unit 90 drives electrodes 100 to apply the enhancement signal to muscle in one area of stomach 20, so as to induce a contraction of the stimulated muscle which, in turn, causes stretching of stretch-receptors in an adjacent portion of the stomach. This form of contraction-mediated stretching simulates the normal appetite-reduction action of the stomach's stretch-receptors, without the patient having eaten the quantities of food which would normally be required to trigger this appetite-reduction response. For example, the control unit may generate an enhancement signal which causes contraction of the corpus of the stomach at the beginning of a meal, whereby a substantial amount of food will accumulate in the fundus. This accumulation, in turn, increases intra-gastric pressure and stretches the fundic walls to a greater extent than would be caused without the applied enhancement signal. If it is determined that a patient has intermittent gastro-esophageal reflux episodes in response to the increased intra-gastric pressure, then it is preferable to additionally apply the enhancement signal to the lower-esophageal sphincter, so as to increase the contraction force thereof and reduce or eliminate the reflux.

Alternatively or additionally, some or all of electrodes 100 are placed in a vicinity of the pyloric sphincter 24 of stomach 20, and control unit 90 drives these electrodes to apply the ETC signal so as to increase a contraction force of the sphincter. Although it is known in the art to apply pacing or other excitatory signals to the sphincter with the intention of contracting the sphincter and increasing the time in which food remains in the stomach, the inventors believe that these prior art methods do not effectively achieve a sufficient level of constriction of the sphincter, and therefore do not engender the optimum weight loss of the patient. By contrast, application of the ETC signal to muscle in the gastrointestinal tract has been shown (see FIG. 3) to substantially increase contraction force above that obtained by pacing alone.

As shown in FIG. 2, digestive activity analysis block 80 typically conveys results of its analysis of the inputs from mechanical sensors 70, supplemental sensors 72, and electrodes 100 to a "parameter search and tuning" block 84 of control unit 90, which iteratively modifies characteristics of the electrical energy applied to stomach 20 in order to attain a desired response. Preferably, operating parameters of block 84 are entered, using operator controls 71, by a physician or other human operator of the control unit. Block 84 typically utilizes multivariate optimization and control methods known in the art in order to cause one or more of the aforementioned mechanical, electrical, chemical and/or other measured parameters to converge to desired values.

In general, each one of electrodes 100 may convey a particular waveform to stomach 20, differing in certain aspects from the waveforms applied by the other electrodes. The particular waveform to be applied by each electrode is determined by control unit 90, preferably under the initial control of the operator. Aspects of the waveforms which are set by the control unit, and may differ from electrode to electrode, typically include parameters such as time shifts between application of waveforms at different electrodes, waveform shapes, amplitudes, DC offsets, durations, and duty cycles. For example, although the waveforms applied to some or all of electrodes 100 usually comprise a train of biphasic square waves following a natural or applied pacing pulse, other waveforms, such as a sinusoid, one or more monophasic square waves, or a waveform including an exponentially-varying characteristic, could be applied to other electrodes. Generally, the shape, magnitude, and timing of the waveforms are optimized for each patient, using suitable optimization algorithms as are known in the art.

Preferably, desired signal parameters are conveyed by block 84 to a signal generation block 86 of control unit 90, which generates, responsive to the parameters, electrical signals that are applied by electrodes 100 to the stomach. Block 86 preferably comprises amplifiers, isolation units, and other standard circuitry known in the art of electrical signal generation.

In an initial calibration procedure, parameter search and tuning block 84 preferably modifies a characteristic (e.g., timing, magnitude, or shape) of the enhancement signal applied through one of electrodes 100, and then determines whether a predetermined response generally improves following the modification. For example, one or more of mechanical sensors 70 may be used to determine the extent to which the shape of stomach 20 changes responsive to corresponding changes in the applied enhancement signal. In a series of similar calibration steps, block 84 repeatedly modifies characteristics of the energy applied through each of the electrodes, such that those modifications that improve the response are generally maintained, and modifications that cause it to worsen are typically eliminated or avoided. Preferably, the calibration procedure is subsequently performed by the physician at intermittent follow-up visits, and/or by unit 90 automatically during regular use of apparatus 18 (e.g., daily).

In a preferred embodiment, the calibration procedure additionally comprises determining a schedule for the application of the enhancement signal at various sites on the stomach. For example, it may be determined for some patients that it is advantageous to: (a) apply the enhancement signal to the sites in a wave, which simulates the natural flow of electrical activity in the stomach, (b) maintain the shape modification for a specified period (e.g., 5–15 minutes), (c) remove the signal for a relaxation period (e.g., 1–5 minutes), and (d) return to step (a).

Preferably, during the initial calibration procedure, the locations of one or more of electrodes 100 are varied while the enhancement signal is applied therethrough, so as to determine optimum placement of the electrodes. In a series of calibration steps, each electrode is moved over an area of stomach 20, and an appropriate response of the stomach is measured. After the physician considers that a sufficient number of sites have been investigated to characterize the area, the electrode is returned to the site yielding the best response. Subsequently, other electrodes, placed on, in, or near the stomach are moved according to the same protocol, so as to achieve substantially optimum placement of some or all of the electrodes.

Based on results of the calibration procedure and/or an analysis of other factors pertaining to the patient's condition, the physician typically determines whether the ETC signal should be applied subsequent to an artificial pacing pulse or in response to natural electrical activity of the stomach. In the former case, the ETC signal is preferably applied in a vicinity of a site where standard gastric pacing pulses are applied. Further preferably, the ETC signal is applied through the same electrode as that through which a gastric pacing pulse is applied.

Alternatively, stomach 20 generates the gastric rhythm, substantially without artificial pacing. In such modes, local sense electrodes 74 and, optionally, some or all of electrodes 100, convey electrical signals to control unit 90, so as to enable parameter search and tuning block 84 to synchronize the electrical signals applied by electrodes 100 with the natural electrical activity of the stomach. It will be understood that although electrodes 74 and 100 are shown for clarity of explanation as separate entities, a single set of electrodes may be used to perform both functions.

Figure 3A:
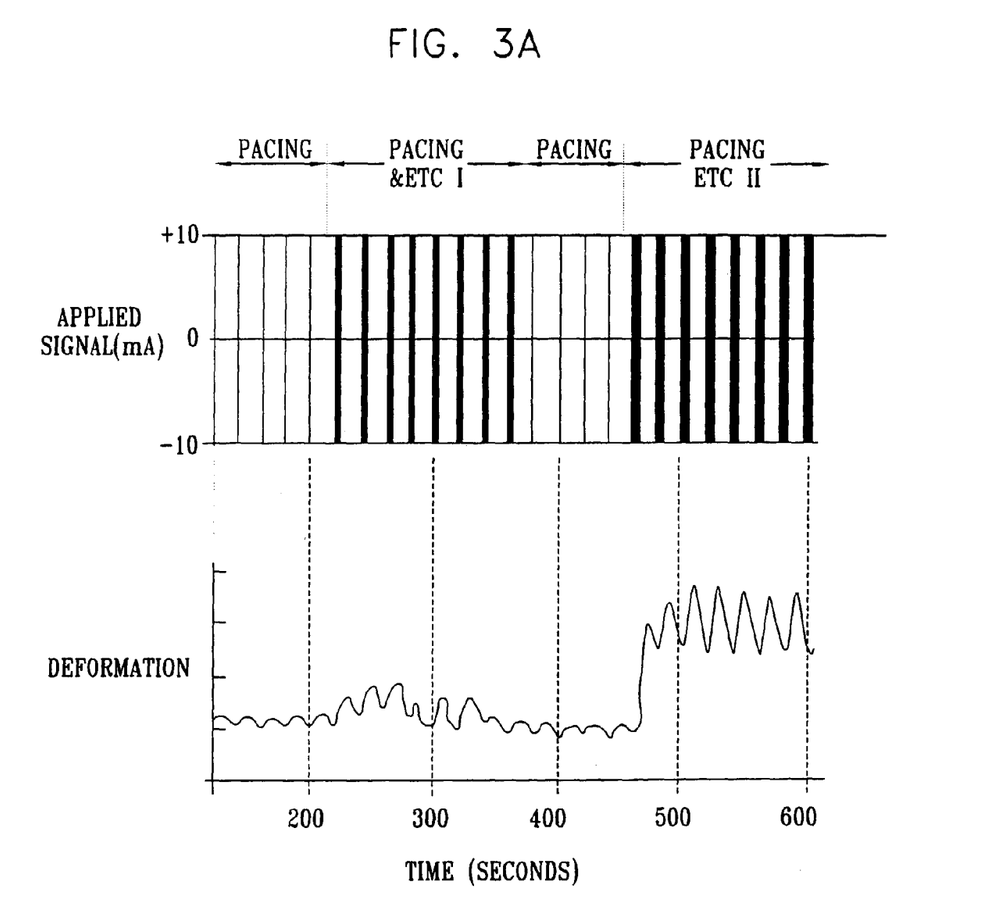
FIG. 3A is a graph showing an electrical signal applied to the stomach of a dog, in accordance with a preferred embodiment of the present invention, and deformations of the stomach produced in response to the applied signal.

FIG. 3A is a graph showing an electrical signal applied to the stomach of a dog, in accordance with a preferred embodiment of the present invention, and deformations of the stomach produced in response to the applied signal. In this experiment, two stitch electrodes were inserted approximately 3 centimeters apart through the serosa of the antral area of the stomach, into the muscularis. Throughout the experiment, the electrodes applied 20 mA peak-to-peak biphasic pacing pulses, each phase lasting for 300 milliseconds. Successive pacing pulses were separated by 20 seconds. In addition, during two periods, ETC signals having characteristics described hereinbelow with reference to FIGS. 3B and 3C were applied following the pacing pulses. The deformation of the outer wall of the stomach responsive to the applied signals was measured continuously by a strain gauge placed on the stomach between the electrodes.

Figure 3B:
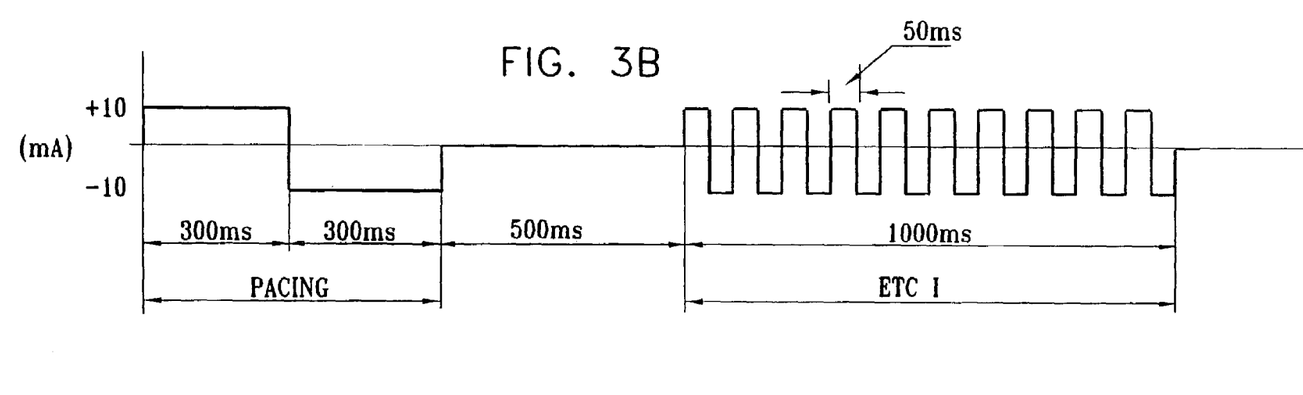
FIGS. 3B and 3C are graphs illustrating details of the electrical signal shown in FIG. 3A, in accordance with respective preferred embodiments of the present invention.
Figure 3C:
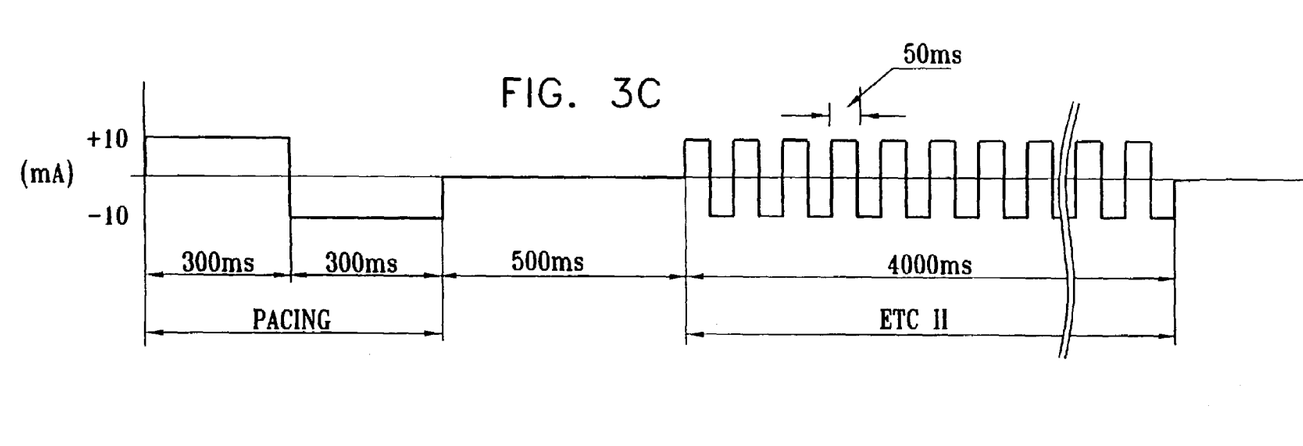

FIGS. 3B and 3C are graphs showing details of the applied pacing pulses and ETC signals shown in FIG. 3A, in accordance with respective preferred embodiments of the present invention. During the period labeled in FIG. 3A, "Pacing & ETC I," an ETC signal lasting 1000 milliseconds was applied starting 500 milliseconds after each pacing pulse. The ETC signal itself comprised a series of biphasic square current pulses (+10 mA, −10 mA), each phase having a 50 millisecond duration. During the period labeled in FIG. 3A, "Pacing & ETC II," an ETC signal having the same parameters was applied to the stomach, except that the duration of the "ETC II" signal application was 4000 milliseconds.

With reference to FIG. 3A, during an approximately two minute warm-up period, small deformations are seen to be produced by each of the pacing pulses. These deformations are believed to generally correspond to the levels of deformation produced due to natural gastric electrical activity. Following this pacing-only warm-up period, the "Pacing & ETC I" signal described hereinabove was applied for about two minutes, during which increased contraction strength by the dog's stomach produced increased deformations, which are clearly visible in FIG. 3A. Subsequently, the "ETC I" signal was removed, and a pacing-only period was recommenced, resulting in a complete return to baseline (pre-ETC) contraction levels. Lastly, during the "Pacing & ETC II" period described hereinabove, deformation of the stomach increased significantly above baseline, and remained significantly above baseline values for the approximately two-minute duration of the signal application. For clinical applications, similar signals are preferably applied through a larger number of electrodes in order to attain and maintain the constriction of the stomach depicted in FIG. 1B.

Figure 4:
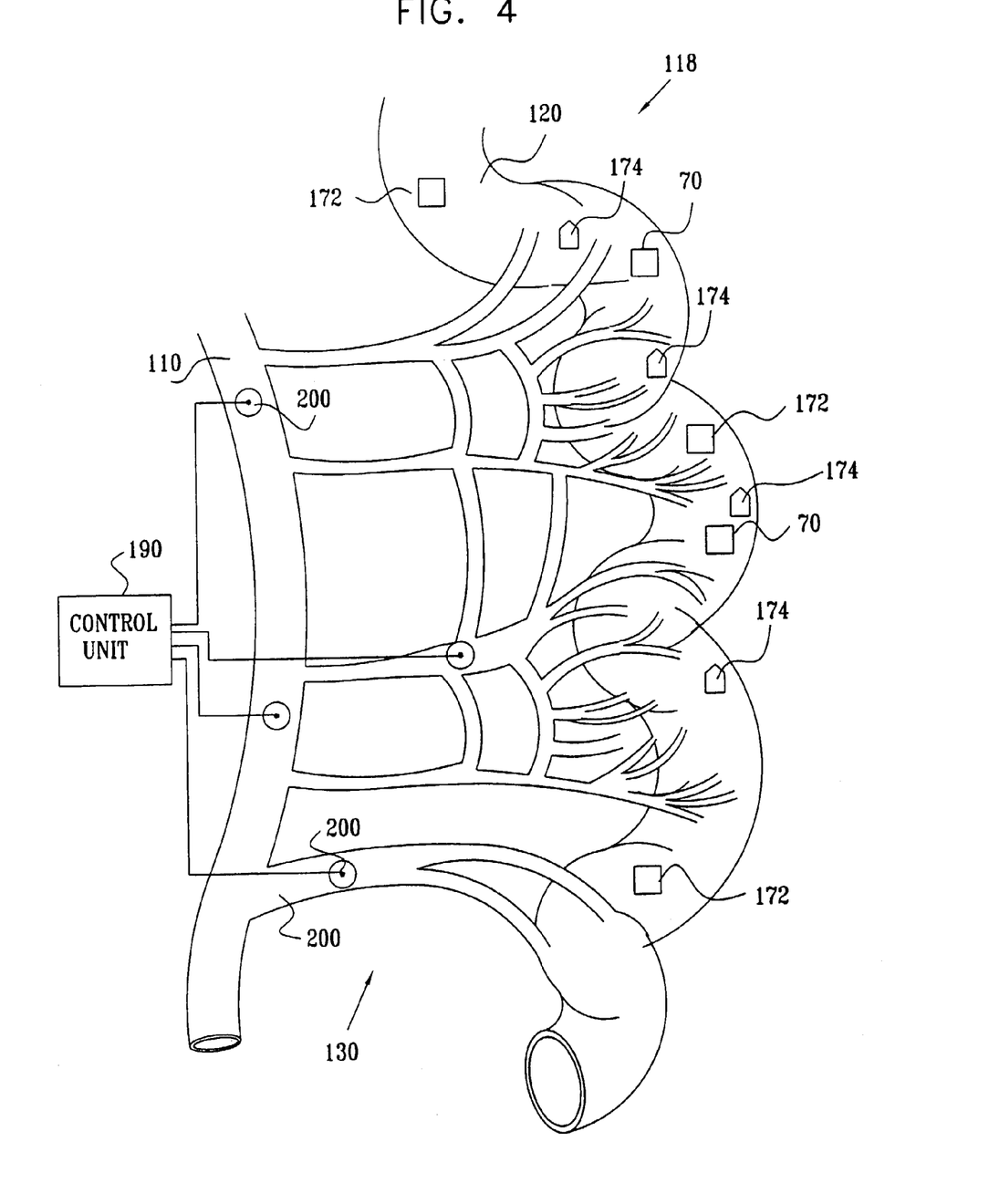
FIG. 4 is a schematic illustration of the vasculature supplying a section of small intestine, showing the placement of electrodes and sensors thereon, in accordance with a preferred embodiment of the present invention.

FIG. 4 is a schematic illustration depicting apparatus 118 for treating obesity or another condition of a patient, in accordance with a preferred embodiment of the present invention. Apparatus 118 preferably comprises a control unit 190, and one or more electrodes 200 applied to or in a vicinity of respective sites of the arterial supply 130 of the patient's small intestine 120. If appropriate, some or all of electrodes 200 may be placed on the superior mesenteric artery 110, or in a vicinity thereof. Typically, control unit 190 drives electrodes 200 to apply signals which cause a controllable level of constriction of the arteries to which these electrodes are coupled. Alternatively or additionally, other transducers (not shown) are implanted in the patient in a vicinity of arterial supply 130, and are driven by control unit 190 to induce some or all of the arteries in supply 130 to contract. As appropriate, these transducers may induce this contraction using mechanical or chemical means. The constriction produced by apparatus 118 preferably transiently and controllably reduces the blood flow to small intestine 120, and thereby reduces the total number of calories which are ultimately absorbed into the patient's bloodstream during and after eating a meal.

For some applications, it is advantageous to utilize apparatus 118 in conjunction with apparatus 18, in order to reduce the patient's weight in a quicker manner than would likely be realized when using either apparatus alone. Alternatively, apparatus 118 may be used without simultaneous use of apparatus 18, for example, if it is determined that the patient is likely to try and "cheat" apparatus 18 by drinking high-calorie liquid foods, whose digestion might not be affected by apparatus 18 to the same extent as that of solid foods. For instance, it is known that many patients who have mechanical gastric-restriction bands drink high-calorie milk-shakes in order to evade the therapeutic effects of the mechanical bands.

Preferably, apparatus and methods described hereinabove with respect to apparatus 18 are utilized, mutatis mutandis, in the operation of apparatus 118. Thus, for example, control unit 190 may drive electrodes 200 to apply an ETC signal and/or pulses and/or other signal forms to modulate arterial supply 130. Additionally, control unit 190 preferably varies parameters of the applied electrical energy responsive to feedback from mechanical sensors 70 and/or supplemental sensors 172, which are typically applied to small intestine 120, in a vicinity thereof, or elsewhere on or in the patient's body.

Preferably, but not necessarily, the electrical energy is applied at times which are likely to produce maximum weight loss, without adversely affecting the patient's nutritional intake, and without significantly reducing the patient's comfort. Thus, for example, one of supplemental sensors 172 may comprise a blood-sugar monitor, which inhibits control unit 190 from applying the electrical energy when the patient's blood sugar is below a determined threshold. Alternatively or additionally, operation of apparatus 118 is initiated or supplemented responsive to a parameter of the contents of small intestine 120, such as an indication by sensors 172 of the lipid concentration thereof. Further alternatively or additionally, the patient is enabled to activate apparatus 118 (e.g., during and after eating dessert, or for a determined time period when the patient is going to sleep) and to deactivate the apparatus (e.g., when the patient has a headache, or has orally taken a medication). Still further alternatively or additionally, apparatus 118 is activated a fixed or variable time (e.g., 10–30 minutes) following initiation of a meal, when it is expected that some digestive products will have reached the small intestine.

Preferably, a calibration period is provided for apparatus 118, which provides some or all of the calibration options described hereinabove with respect to apparatus 18. In addition, safe signal application durations and activation sequences of electrodes 200 are preferably determined during the calibration period, such that small intestine 120 continually has a sufficient level of blood flowing therethrough to support normal activity of the tissue of the small intestine.

For some applications, an intestinal enhancement signal is applied to electrodes 174 coupled to respective sites on small intestine 120. Preferably, control unit 190 drives electrodes 174 to apply the intestinal enhancement signal so as to increase the contraction force generated by muscle of small intestine 120. This increased contraction force, in turn, decreases the period of time in which digestion products remain in the intestine, and, therefore, decreases the quantity of these digestion products which are ultimately absorbed into the patient's bloodstream. As appropriate, the intestinal enhancement signal may comprise an ETC component and/or other signals known in the art for stimulating tissue. Moreover, the intestinal enhancement signal may be applied in combination with, or separately from, the signals applied to electrodes 100 and/or 200, described hereinabove.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. Apparatus for treating a condition, comprising:
    a set of one or more electrodes, adapted to be applied to one or more respective sites in a vicinity of a stomach of a patient; and
    a control unit, adapted to drive the electrode set to apply an Excitable-Tissue Control (ETC) signal to the sites, configured such that application thereof decreases a cross-sectional area of at least a portion of the stomach, wherein the control unit is adapted to configure a timing parameter of the ETC signal responsive to timing of natural gastric electrical activity.

2. Apparatus according to claim 1, wherein the electrode set is adapted to be applied in contact with muscle tissue of the stomach.

3. Apparatus according to claim 1, wherein the control unit is adapted to configure the ETC signal such that application thereof decreases a volume of the stomach.

4. Apparatus according to claim 1, wherein the control unit is adapted to drive the electrode set to apply the ETC signal as a series of biphasic pulses.

5. Apparatus according to claim 1, wherein the control unit is adapted to configure the ETC signal to have a duration of at least about 1 second.

6. Apparatus according to claim 5, wherein the control unit is adapted to configure the ETC signal to have a duration of at least about 3 seconds.

7. Apparatus according to claim 1, wherein the control unit is adapted to drive the electrode set in accordance with a schedule programmed into the control unit.

8. Apparatus for treating a condition, comprising:
    a set of one or more electrodes, adapted to be applied to one or more respective sites in a vicinity of a stomach of a patient; and
    a control unit, adapted to drive the electrode set to apply an Excitable-Tissue Control (ETC) signal to the sites, configured such that application thereof decreases a cross-sectional area of at least a portion of the stomach, wherein the control unit is adapted to receive a patient signal, input by the patient, and to drive the electrode set responsive to the patient signal.

9. Apparatus according to claim 8, wherein the electrode set is adapted to be applied in contact with muscle tissue of the stomach.

10. Apparatus according to claim 8, wherein the control unit is adapted to configure the ETC signal such that application thereof decreases a volume of the stomach.

11. Apparatus according to claim 8, wherein the control unit is adapted to drive the electrode set to apply the ETC signal as a series of biphasic pulses.

12. Apparatus according to claim 8, wherein the control unit is adapted to configure the ETC signal to have a duration of at least about 1 second.

13. Apparatus according to claim 12, wherein the control unit is adapted to configure the ETC signal to have a duration of at least about 3 seconds.

14. Apparatus according to claim 8, wherein the control unit is adapted to drive the electrode set in accordance with a schedule programmed into the control unit.

15. Apparatus for treating a condition, comprising:
    a set of one or more electrodes, adapted to be applied to one or more respective sites in a vicinity of a stomach of a patient;
    a control unit, adapted to drive the electrode set to apply an Excitable-Tissue Control (ETC) signal to the sites, configured such that application thereof decreases a cross-sectional area of at least a portion of the stomach; and
    a second set of one or more electrodes, adapted to be applied to one or more respective sites in a vicinity of a lower-esophageal sphincter of the patient, wherein the control unit is adapted to drive the second electrode set to apply a sphincter-control signal to the sphincter, configured such that application thereof increases a contraction force generated by the sphincter.

16. Apparatus for treating a condition, comprising:
    exactly one set of one or more electrodes, adapted to be applied to one or more respective sites in a vicinity of a body of a stomach of a patient, the one or more respective sites generally arranged in a plane substantially perpendicular to a longitudinal axis of the stomach; and
    a control unit, adapted to drive the electrode set to apply to the body of the stomach, substantially in the plane, a signal configured such that application thereof increases a level of contraction of muscle tissue of the body of the stomach, and decreases a cross-sectional area of a portion of the body of the stomach substantially in the plane for a substantially continuous period greater than about 3 seconds.

17. Apparatus according to claim 16, wherein the electrode set is adapted to be applied in contact with muscle tissue of the stomach.

18. Apparatus according to claim 16, wherein the control unit is adapted to configure the signal such that application thereof decreases a volume of the stomach.

19. Apparatus according to claim 16, wherein the control unit is adapted to drive the electrode set in accordance with a schedule programmed into the control unit.

20. A method for treating a condition, comprising:
    applying an Excitable-Tissue Control (ETC) signal to one or more sites in a vicinity of a stomach of a patient; and
    configuring the ETC signal such that application thereof to the one or more sites decreases a cross-sectional area of at least a portion of the stomach,
    wherein configuring the signal comprises configuring a timing parameter of the signal responsive to timing of natural gastric electrical activity.

21. A method according to claim 20, wherein applying the signal comprises applying the signal to muscle tissue of the stomach.

22. A method according to claim 20, wherein configuring the signal comprises configuring the signal such that application thereof decreases a volume of the stomach.

23. A method according to claim 20, wherein configuring the signal comprises configuring the signal as a series of biphasic pulses.

24. A method according to claim 20, wherein configuring the signal comprises configuring the signal to have a duration of at least about 1 second.

25. A method according to claim 24, wherein configuring the signal comprises configuring the signal to have a duration of at least about 3 seconds.

26. A method according to claim 20, wherein configuring the signal comprises configuring the signal in accordance with a schedule.

27. A method for treating a condition, comprising:
applying an Excitable-Tissue Control (ETC) signal to one or more sites in a vicinity of a stomach of a patient;
configuring the ETC signal such that application thereof to the one or more sites decreases a cross-sectional area of at least a portion of the stomach;
applying a sphincter-control signal to one or more sites in a vicinity of a lower-esophageal sphincter of the patient; and
configuring the sphincter-control signal such that application thereof increases a contraction force generated by the sphincter.

28. A method for treating a condition, comprising:
applying an Excitable-Tissue Control (ETC) signal to one or more sites in a vicinity of a stomach of a patient;
configuring the ETC signal such that application thereof to the one or more sites decreases a cross-sectional area of at least a portion of the stomach; and
receiving a patient signal input by the patient, wherein configuring the ETC signal comprises configuring the ETC signal responsive to the patient signal.

29. A method according to claim 28, wherein applying the signal comprises applying the signal to muscle tissue of the stomach.

30. A method according to claim 28, wherein configuring the signal comprises configuring the signal such that application thereof decreases a volume of the stomach.

31. A method according to claim 28, wherein configuring the signal comprises configuring the signal as a series of biphasic pulses.

32. A method according to claim 28, wherein configuring the signal comprises configuring the signal to have a duration of at least about 1 second.

33. A method according to claim 32, wherein configuring the signal comprises configuring the signal to have a duration of at least about 3 seconds.

34. A method according to claim 28, wherein configuring the signal comprises configuring the signal in accordance with a schedule.

35. A method for treating a condition, comprising:
applying a signal to exactly one set of one or more sites in a vicinity of a body of a stomach of a patient, the one or more sites generally arranged in a plane substantially perpendicular to a longitudinal axis of the stomach; and
configuring the signal such that application thereof to the one or more sites increases a level of contraction of muscle tissue of a portion of the body of the stomach substantially in the plane, and decreases a cross-sectional area of the portion for a substantially continuous period greater than about 3 seconds.

36. A method according to claim 35, wherein applying the signal comprises applying the signal to muscle tissue of the body of the stomach.

37. A method according to claim 35, wherein configuring the signal comprises configuring the signal such that application thereof decreases a volume of the body of the stomach.

38. A method according to claim 35, wherein configuring the signal comprises configuring the signal in accordance with a schedule.

* * * * *